United States Patent
Sun et al.

(10) Patent No.: US 9,408,384 B2
(45) Date of Patent: *Aug. 9, 2016

(54) WATER-SOLUBLE GRANULE FORMULATION OF 2,4-D SALT AND PREPARATION METHOD THEREOF

(75) Inventors: Guoqing Sun, Weifang (CN); Yongsheng Hou, Weifang (CN); Yong Wu, Weifang (CN); Liwei Xu, Weifang (CN); Shuai Chen, Weifang (CN)

(73) Assignee: Shandong Weifang Rainbow Chemical Co., Ltd., Weifang, Shandong Province (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/119,503

(22) PCT Filed: May 2, 2012

(86) PCT No.: PCT/CN2012/000582
§ 371 (c)(1),
(2), (4) Date: Nov. 22, 2013

(87) PCT Pub. No.: WO2013/106972
PCT Pub. Date: Jul. 25, 2013

(65) Prior Publication Data
US 2014/0323308 A1  Oct. 30, 2014

(30) Foreign Application Priority Data
Jan. 19, 2012  (CN) .......................... 2012 1 0016942

(51) Int. Cl.
*A01N 39/02*  (2006.01)
*A01N 39/04*  (2006.01)
*A01N 37/38*  (2006.01)

(52) U.S. Cl.
CPC ................ *A01N 37/38* (2013.01); *A01N 39/04* (2013.01)

(58) Field of Classification Search
CPC .............................. A01N 37/36; A01N 39/04
See application file for complete search history.

(56) References Cited

U.S. PATENT DOCUMENTS

| | | | |
|---|---|---|---|
| 5,441,923 A | 8/1995 | Tocker | |
| 6,022,829 A * | 2/2000 | Mito | ............................. 504/134 |
| 6,387,388 B1 | 5/2002 | Misselbrook et al. | |
| 6,579,831 B1 | 6/2003 | Harwell | |
| 7,094,734 B2 | 8/2006 | Ushiguchi et al. | |
| 7,883,715 B2 * | 2/2011 | Abraham et al. | ............. 424/405 |
| 2010/0248962 A1 | 9/2010 | Wilczynski | |

FOREIGN PATENT DOCUMENTS

| | | |
|---|---|---|
| CN | 1040728 | 3/1990 |
| CN | 1206330 | 1/1999 |
| CN | 1537427 | 10/2004 |
| CN | 1608465 | 4/2005 |
| CN | 101326918 | 12/2008 |
| CN | 101690498 | 4/2010 |
| CN | 102301997 | 1/2012 |
| JP | 2011201780 | 10/2011 |

OTHER PUBLICATIONS

CN 102301997A, Wei et al. machine translation of One kind of 2,4-D particle herbicidal compound and preparation method, 1997.*
Li, Chunx, "Study of weeding non-arable weeds by 90% drop acid Ammonium glyphosate soluble granules", Shanghai Agricultural Science and Technology, 2011, 4.
Song, Bin, "Study on Weed Control of 56% MCPA-Na SP in Wheat Field", Journal of Anhui Agricultural Sciences, Jun. 25, 2004, 32(3):466.
Yuan, Huifu et al., "Screening of the Weed Killerin the Naked Oats Field of the Hebei Northwest Region", Journal of Henan Agricultural Sciences, Nov. 15, 2009, 11:90-93.
International Search Report for PCT/CN2012/000582 dated Oct. 15, 2012.

* cited by examiner

*Primary Examiner* — Alton Pryor
(74) *Attorney, Agent, or Firm* — Andrus Intellectual Property Law, LLP

(57) ABSTRACT

The present invention discloses a water-soluble granule formulation of 2,4-D salt, comprising components in the following weight percent: 5-80% 2,4-D salt (calculated as 2,4-D acid), and a water-soluble filler as the balance. The water-soluble granule formulation of 2,4-D salt has an outstanding control efficiency on annual or perennial Poaceae weeds and some broadleaf weeds in fields of soybean and other Fabaceae plants, for example, such weeds as amaranth, knotweed, lamb's-quarters night shade, siberian cocklebur, barnyard grass, foxtail grass, digitaria sanguinalis, broomcorn millet and the like. The formulation is environment-friendly, and has the advantages of being free of organic solvents and dusts and being easy to measure in comparison to conventional emulsifiable formulation, wettable powder formulation and suspension formulation. The present invention also discloses the preparation method of the formulation. The production process is simple, economical and safe. The whole production process, without the use of dangerous chemicals, is easy to control and operate and has a high safety factor.

13 Claims, No Drawings

WATER-SOLUBLE GRANULE FORMULATION OF 2,4-D SALT AND PREPARATION METHOD THEREOF

CROSS REFERENCE TO RELATED APPLICATION

The present application is the U.S. national stage of International Application PCT/CN2012/000582, filed May 2, 2012, which international application was published on Jul. 25, 2013, as International Publication No. WO2013/106972. The International Application claims priority to Chinese Patent Application No. 201210016942.X, filed Jan. 19, 2012, the contents of which are incorporated herein by reference in their entireties.

TECHNICAL FIELD

The present invention relates to a herbicide and a preparation method thereof and in particular to a water-soluble granule formulation of 2,4-D salt (i.e. water-soluble granule) and a preparation method thereof.

BACKGROUND ART 2,4-D, a phenoxyalkanoic acids herbicide, is a selective systemic hormone herbicide. Pure 2,4-D exists as white crystals, which has low solubility in water but is easily soluble in organic solvents such as ethanol and benzene. The amine salts and sodium salts of 2,4-D, however, are quite easily soluble in water. 2,4-D is strongly systemic. At low concentration, 2,4-D can inhibit the growth and development of the plant and cause uncontrolled growth and eventually death. 2,4-D is mainly used for post-emergence foliar treatment and has various effects on the synthesis of nucleic acids and proteins, such that the growing points of the plant stop growing, young leaves are inextensible and normal photosynthesis is inhibited. When transported to the lower parts of the plants, 2,4-D can promote uncontrolled cell division. Root tips become swollen, losing the ability of absorption. Stems and stalks become distorted and aberrant. Sieve tubes are blocked and the phloem is damaged, such that the transport of organic substances is obstructed, leading to the death of the plant. 2,4-D herbicide has an outstanding control efficiency on annual or perennial Poaceae weeds and some broadleaf weeds in fields of soybean and other Fabaceae plants, for example, such weeds as amaranth, knotweed, lamb's-quarters, night shade, siberian cocklebur, barnyard grass, foxtail grass, digitaria sanguinalis, broomcorn millet and the like.

The main formulations of 2,4-D are emulsifiable formulation of its esters and aqueous formulation of its salts. Because the organic solvents in the emulsifiable formulation are flammable and would cause great pollution to the environment, the fraction of such formulation among herbicide formulations has been decreasing annually in recent years. Although aqueous formulation of 2,4-D salt is environment-friendly, the aqueous formulation with high concentration is very easy to crystallize at low temperatures, and the aqueous formulation with low concentration, while easy to crystallize, will lead to increased costs in packaging and transporting, which limits the use of aqueous formulation of 2,4-D salt to some extent.

SUMMARY OF THE INVENTION

In order to overcome the disadvantages of the prior art, the present invention provides a water-soluble granule formulation of 2,4-D salt which is simple in components, friendly to the environment, and more convenient for application than other existing formulations.

The present invention further provides a preparation method of the water-soluble granule formulation whereby 2,4-D salt is readily made into water-soluble granules, with simple granulation and convenient operation.

The present invention is achieved by the following, technical solution:

A water-soluble granule formulation of 2,4-D salt, comprising components in the following weight percent: 5-80% 2,4-D salt (calculated as 2,4-D acid), and a water-soluble filler which is used to make up to 100%.

In the above-mentioned water-soluble granule formulation of 2,4-D salt, the 2,4-D salt is selected from one or more of isopropylamine salt, ethylamine salt, monomethylamine salt, dimethylamine salt, sodium salt, potassium salt and ammonium salt.

In the above-mentioned water-soluble granule formulation of 2,4-D salt, only a water-soluble filler is needed to prepare water-soluble granules, without the need to add any surfactant and binder. The used water-soluble filler is a water-soluble inorganic salt which is selected from one or more of sulfate, nitrate, hydrochlorate, carbonate, bicarbonate, phosphate, dibasic phosphate, monobasic phosphate, borate and silicate.

In the above-mentioned water-soluble granule formulation of 2,4-D salt, the water-soluble inorganic salts used can be mixed in any ratio.

2,4-D salt herbicide is made into water dispersible granule formulation in the present invention, which overcomes the disadvantages existing, in the aqueous formulation and makes the application of the herbicide more convenient. The water dispersible granule formulation of the present invention is simpler in components, without the need to add excipient component such as surfactant, binder and the like. Nevertheless, 2,4-D salt is hard to granulate without adding surfactant or binder. Therefore, based on the composition of the water-soluble granule formulation, the present invention provides a method suitable for preparing the formulation which allows easy granulation and convenient operation.

The preparation method of the present invention comprises: sufficiently and homogeneously mixing the 2,4-D salt and the water-soluble filler in a kneader, adding 1-10 wt % water based on the total amount of the 2,4-D salt and the water-soluble filler to perform kneading, granulating at 40-110° C. after kneading, and drying at 20-90° C.

In the above-mentioned preparation method, granulation is performed without adding any binder and surfactant, so long as it is ensured that the mixture is granulated at 40-110° C.

In comparison with the prior art, the water-soluble granule formulation of 2,4-D salt of the present invention has the following advantages:

1. The production process is simple, economical and safe. The whole production process, without the use of dangerous chemicals, is easy to control and operate and has a high safety factor.

2. The water-soluble granule formulation is environment-friendly, and has the advantages of being free of organic solvents and dusts and being easy to measure in comparison to conventional emulsifiable formulation, wettable powder formulation and suspension formulation.

3. The water-soluble granule formulation of 2,4-D salt obtained is convenient for using, which reduces the costs of packaging, storing and transporting and is suitable for large-scale popularization and application.

DETAILED DESCRIPTION OF THE INVENTION

Hereinafter further description will be made by incorporating examples to illustrate the present invention, which by no means should be regarded as a limitation of the present invention.

Example 1

The content (by weight) of each component was: 65% 2,4-D dimethylamine salt (calculated as 2,4-D acid), and ammonium phosphate monobasic and sodium phosphate dibasic which were used to make up to 100%. The components were sufficiently and homogeneously mixed in a kneader. Then 5% water was added to perform kneading followed by granulating at 55° C., drying at 82° C. Thus a water-soluble granule formulation of 65% 2,4-D dimethylamine salt (calculated as 2,4-D acid) was obtained.

Example 2

The content (by weight) of each component was: 50% 2,4-D monomethylamine salt (calculated as 2,4-D acid), and water-soluble inorganic salt ammonium nitrate which was used to make up to 100%. The components were sufficiently and homogeneously mixed in a kneader. Then 1% water was added to perform kneading followed by granulating at 70° C., drying at 74° C. Thus a water-soluble granule formulation of 50% 2,4-D dimethylamine salt (calculated as 2,4-D acid) was obtained.

Example 3

The content (by weight) of each component was: 5% 2,4-D ethylamine salt (calculated as 2,4-D acid), and water-soluble inorganic, salt ammonium chloride which was used to make up to 100%. The components were sufficiently and homogeneously mixed in a kneader. Then 7% water was added to perform kneading followed by granulating at 40° C., drying at 65° C. Thus a water-soluble granule formulation of 5% 2,4-D ethylamine salt (calculated as 2,4-D acid) was obtained.

Example 4

The content (by weight) of each component was: 20% 2,4-D potassium salt (calculated as 2,4-D acid), and water-soluble inorganic salt potassium phosphate which was used to make up to 100%. The components were sufficiently and homogeneously mixed in a kneader. Then 10% water was added to perform kneading followed by granulating at 100° C., drying at 20° C. Thus a water-soluble granule formulation of 20% 2,4-D ethylamine potassium salt (calculated as 2,4-D acid) was obtained.

Example 5

The content (by weight) of each component was: 35% 2,4-D potassium salt (calculated as 2,4-D acid), and water-soluble inorganic salts sodium bicarbonate and sodium carbonate which were used to make up to 100%. The components were sufficiently and homogeneously mixed in a kneader. Then 3% water was added to perform kneading followed by granulating at 95° C., drying at 43° C. Thus a water-soluble granule formulation of 35% 2,4-D ethylamine amine salt (calculated as 2,4-D acid) was obtained.

Example 6

The content (by weight) of each component was: 80% 2,4-D isopropylamine salt, and water-soluble inorganic salts anhydrous sodium sulfate and dibasic sodium phosphate which were used to make up to 100%. The components were sufficiently and homogeneously mixed in a kneader. Then 4% water was added to perform kneading followed by granulating at 85° C., drying at 90° C. Thus a water-soluble granule formulation of 80% 2,4-D isopropylamine salt was obtained.

INDUSTRIAL APPLICABILITY

The prepared water-soluble granule formulation of the present invention is free of organic solvents and dusts, and is friendly to the environment. The water-soluble granule formulation has a remarkable effect when it is used to remove annual and perennial Poaceae weeds and some broadleaf weeds in fields of soybean and other Fabaceae plants, such weeds as amaranth, knotweed, lamb's-quarters, night shade, siberian cocklebur, barnyard grass, foxtail grass, digitaria sanguinalis and the like, which is more convenient for application compared with other existing formulations and has industrial applicability.

The invention claimed is:

1. A water-soluble granule formulation of 2,4-D salt consisting essentially of 5-80% 2,4-D salt (calculated as 2,4-D acid) as the only active ingredient, and a water-soluble filler as the balance to 100%, wherein the formulation does not include any surfactant nor binder, wherein the 2,4-D salt is the only herbicide in the formulation.

2. The water-soluble granule formulation of 2,4-D salt according to claim 1 consisting essentially of 50-80% 2,4-D salt (calculated as 2,4-D acid) as the only active ingredient, and the water-soluble filler as the balance to 100%.

3. The water-soluble granule formulation of 2,4-D salt according to claim 1 consisting essentially of 65-80% 2,4-D salt (calculated as 2,4-D acid) as the only active ingredient, and the water-soluble filler as the balance to 100%.

4. The water-soluble granule formulation of 2,4-D salt according to claim 1 consisting essentially of 80% 2,4-D salt (calculated as 2,4-D acid) as the only active ingredient, and the water-soluble filler as the balance to 100%.

5. The water-soluble granule formulation of 2,4-D salt according to claim 1, wherein said 2,4-D salt is selected from one or more of isopropylamine salt, ethylamine salt, monomethylamine salt, dimethylamine salt, sodium salt, potassium salt and ammonium salt.

6. The water-soluble granule formulation of 2,4-D salt according to claim 5, wherein said 2,4-D salt is dimethylamine salt.

7. The water-soluble granule formulation of 2,4-D cording to claim 1, characterized in that said water-soluble filler is a water-soluble inorganic salt.

8. The water-soluble granule formulation of 2,4-D salt according to claim 7, wherein said water-soluble inorganic salt is selected from one or more of sulfate, nitrate, hydrochlorate, carbonate, bicarbonate, phosphate, dibasic phosphate, monobasic phosphate, borate and silicate.

9. The water-soluble granule formulation of 2,4-D salt according to claim 8, wherein said water-soluble inorganic salt is a mixture of water-insoluble inorganic salts.

10. The water-soluble granule formulation of 2,4-D salt according to claim 1 consisting essentially of 65% 2,4-D dimethylamine salt (calculated as 2,4-D acid) as the only active ingredient, and ammonium phosphate monobasic and sodium phosphate dibasic as the water-soluble fillers which are used to make up the balance to 100%, and the formulation is prepared by a method wherein the components are sufficiently and homogeneously mixed in a kneader, then 5% water is added to perform kneading followed by granulating at 55° C., drying at 82° C., thus a water-soluble granule formulation of 65% 2,4-D dimethylamine salt (calculated as 2,4-D acid) is obtained.

11. The water-soluble granule formulation of 2,4-D salt according to claim 1 consisting essentially of 80% 2,4-D isopropylamine salt (calculated as 2,4-D acid) as the only active ingredient, and water-soluble inorganic salts anhydrous sodium sulfate and dibasic sodium phosphate as the water-soluble fillers which are used to make up the balance to 100%, and the formulation is prepared by a method wherein the components are sufficiently and homogeneously mixed in a kneader, then 4% water is added to perform kneading followed by granulating at 85° C., drying at 90° C., thus a water-soluble granule formulation of 80% 2,4-D isopropylamine salt (calculated as 2,4-D acid) is obtained.

12. A preparation method of the water-soluble granule formulation of 2,4-D salt according to claim 1, wherein said water-soluble granule formulation of 2,4-D salt is prepared by homogeneously mixing the 2,4-D salt and the water-soluble filler according to ratio and performing granulation at 40-110° C.

13. The preparation method according to claim 12, wherein said preparation method comprises the following steps: sufficiently mixing the 2,4-D salt and the water-soluble filler in a kneader, adding 1-10 wt % water to perform kneading, granulating at 40-110° C. after kneading, and drying at 20-90° C. to obtain the water-soluble granule formulation of 2,4-D salt.

* * * * *